US007843330B2

(12) United States Patent
Chamberlain et al.

(10) Patent No.: US 7,843,330 B2
(45) Date of Patent: Nov. 30, 2010

(54) INTERACTIVE PATIENT MANAGEMENT SYSTEM AND METHOD

(75) Inventors: Forrest Chamberlain, South Burlington, VT (US); Tracy Hunter, Waukesha, WI (US); Manjri Patel, Crystal Lake, IL (US); Christopher Lindop, Brookfield, WI (US)

(73) Assignee: General Electric Company, Schenectady, NY (US)

( * ) Notice: Subject to any disclaimer, the term of this patent is extended or adjusted under 35 U.S.C. 154(b) by 343 days.

(21) Appl. No.: 12/103,541

(22) Filed: Apr. 15, 2008

(65) Prior Publication Data

US 2009/0256701 A1 Oct. 15, 2009

(51) Int. Cl.
*G08B 1/08* (2006.01)

(52) U.S. Cl. .............................. 340/539.12; 340/825.49; 340/573.1; 340/568.1

(58) Field of Classification Search ............. 340/539.12, 340/539.1, 568.1, 572.1–572.9, 539.13, 825.49, 340/825.52, 825.69, 573.1, 286.07
See application file for complete search history.

(56) References Cited

U.S. PATENT DOCUMENTS 5,760,704 A * 6/1998 Barton et al. .......... 340/825.49

| 5,822,544 | A | * | 10/1998 | Chaco et al. .................. 705/2 |
|---|---|---|---|---|
| 6,023,631 | A | * | 2/2000 | Cartmell et al. ............. 600/372 |
| 6,024,699 | A | * | 2/2000 | Surwit et al. ................ 600/300 |
| 7,251,683 | B1 | | 7/2007 | Shah |
| 7,269,427 | B2 | * | 9/2007 | Hoctor et al. ............ 455/456.2 |
| 7,443,302 | B2 | * | 10/2008 | Reeder et al. ............. 340/573.1 |
| 7,636,445 | B2 | * | 12/2009 | Yoshimine .................. 381/67 |
| 2004/0170154 | A1 | * | 9/2004 | Carter et al. ................ 370/338 |
| 2005/0261942 | A1 | * | 11/2005 | Wheeler ........................ 705/3 |
| 2008/0303638 | A1 | * | 12/2008 | Nguyen et al. ........... 340/10.42 |

* cited by examiner

*Primary Examiner*—Daniel Previl
(74) *Attorney, Agent, or Firm*—McAndrews, Held & Malloy, Ltd.; Michael A. Dellapenna

(57) ABSTRACT

Certain embodiments of the present invention provide a mobile device configured to instruct and direct a patient within a medical care facility. The medical device may include a main housing configured to be conveyed by the patient within the medical care facility, a display positioned on the main housing, a tracking device configured to be tracked by a patient information system, a processor in communication with the display, and a transceiver allowing bi-directional communication between the mobile device and the patient information system. The transceiver may be configured to receive patient-specific directions and instructions regarding a medical care event that are transmitted from the patient information system. The processor is operable to show the patient-specific directions and instructions on the display.

27 Claims, 3 Drawing Sheets

INTERACTIVE PATIENT MANAGEMENT SYSTEM AND METHOD

BACKGROUND OF THE INVENTION

Embodiments of the present invention generally relate to a system and method of managing and directing a patient within a medial facility, and more particularly, to an interactive wireless device that is configured to provide bidirectional communication between a patient and a care provider.

Many individuals are nervous, and often confused, when arriving at a medical care facility, such as a hospital, for a particular procedure, check-up or the like. Upon arrival at the medical care facility, many patients may be confused as to the exact location where a particular procedure is to take place. As such, a patient may become lost and frustrated, thereby delaying the procedure and increasing the patient's anxiety. Moreover, the patient may find that he/she is lost and/or frustrated while attempting to navigate within the institution, even after he/she initially arrives.

When the patient does arrive at the proper location, the patient typically manually completes information forms. Completing these forms, including insurance forms, takes time. Once the forms are completed, an employee of the medical care facility typically inputs this information into a central database. This process, however, may be susceptible to erroneous input of information, such as if the employee misreads a portion of the form and/or inputs a typographical error. In short, entry of patient information using paper systems is error prone and requires redundant data entry.

Additionally, many patients experience emergencies and need to notify providers quickly. For example, a patient may fall down and injure him/herself while in the facility. Typically, the patient needs to contact someone, such as by calling for help, or by contacting someone through a telephone. However, the patient may not be able to find a telephone, or even gain access to one. Moreover, the patient may be too weak to effectively yell for assistance.

Sometimes, when patients arrive at a proper location for a procedure, the care providers mix up patient records. For example, a portion of one patient's paper file may be inadvertently intermingled with another patient's paper file. In such circumstances, the care provider needs additional time to sort through the confusion, thereby making the process inefficient. At worst, a care provider may provide improper diagnoses and/or prognoses based on mixed up records.

Further, a patient may need to visit multiple locations within a medical facility. For example, a patient may be initially checked by a doctor at a first location, and then need to visit a radiology lab for x-rays. In such situations, the patient may become lost when trying to find the second location. Additionally, the care provider may decide that it is best for the patient to visit another location after the patient's check-up, but after the patient has left the doctor's office. In this situation, it is difficult for the care provider to alert the patient of the change of location.

Also, many patients may not be able to read the signs within a medical care facility. For example, a patient who is not entirely fluent with a particular language may have difficulty reading the direction signs within a medical care facility if those signs are not in the patient's fluent language.

BRIEF SUMMARY OF THE INVENTION

Certain embodiments of the present invention provide a mobile device configured to instruct and direct a patient within a medical care facility. The mobile device may include a main housing configured to be conveyed by the patient within the medical care facility, a display positioned on the main housing, a tracking device, such as an RFID tag, configured to be tracked by a patient information system, a processor in communication with the display, and a transceiver allowing bi-directional communication between the mobile device and the patient information system. The transceiver is configured to receive patient-specific directions and instructions regarding a medical care event that are transmitted from the patient information system. The processor is operable to show the patient-specific directions and instructions on the display. The patient-specific directions and instructions are updated based on a tracked location of the mobile device. The process is also operable to show a patient name and identification number on the display The display may include a touch-screen that is configured to allow the patient to make selections by touching virtual buttons on the touch-screen. The mobile device may also include a plurality of actual buttons, such as membrane switches located on the housing, or virtual buttons, such as would appear on the touch screen. One such button may be a directions button configured to allow the patient to acquire directions to a particular location, such as the nearest restroom, within the medical care facility. Another button may be menu button that allows a patient to view and/or cycle through a plurality of options. Another button may be a call button that allows the patient to directly contact medical personnel. Further, an emergency button may allow the patient to inform the medical personnel of an immediate emergency. Additionally, embodiments of the present invention may provide and display special instructions, such as dietary restrictions before a procedure, to a patient.

Certain embodiments of the present invention also provide a system configured to instruct and direct a patient within a medical care facility. The system may include a patient information subsystem and a mobile device.

The patient information subsystem may include a central processing unit, a patient database in communication with the central processing unit, a tracking subsystem in communication with the central processing unit, and a first transceiver in communication with the central processing unit.

The mobile device is configured to be conveyed by the patient within the medical care facility. The mobile device is separate and distinct from the patient information subsystem. The mobile device may include a display positioned on the main housing, a tracking device configured to be tracked by the tracking subsystem, a processor in communication with the display, and a second transceiver allowing bidirectional communication between the mobile device and the patient information system. The second transceiver receives patient-specific directions and instructions regarding a medical care event that are transmitted from the central processing unit through the first transceiver. The processor is operable to show the patient-specific directions and instructions received from the patient information subsystem on the display.

Certain embodiments of the present invention provide a method of instructing and directing a patient within a medical care facility with respect to a medical care event. The method may include matching patient information input by the patient into a mobile device with data stored in a patient information system that is separate and distinct from the mobile device, transmitting instructions and directions from the patient information system to the mobile device based on the matching, displaying the instructions and directions on the mobile device, and updating the instructions and directions based on one or both of the location of the patient within the medical care facility and/or a stage of the medical care event (e.g., whether a particular medical care event, such as an x-ray procedure, is completed).

The method may also include receiving personal and insurance information directly input by the patient into the mobile device at the patient information system. The method may also include automatically registering the patient for the medical care event when the patient arrives at the proper location and after the receiving. The method may also include alerting the patient to return the mobile device when the patient moves out of a predetermined area (e.g., locations proximate exits of the medical care facility).

Figure 1:
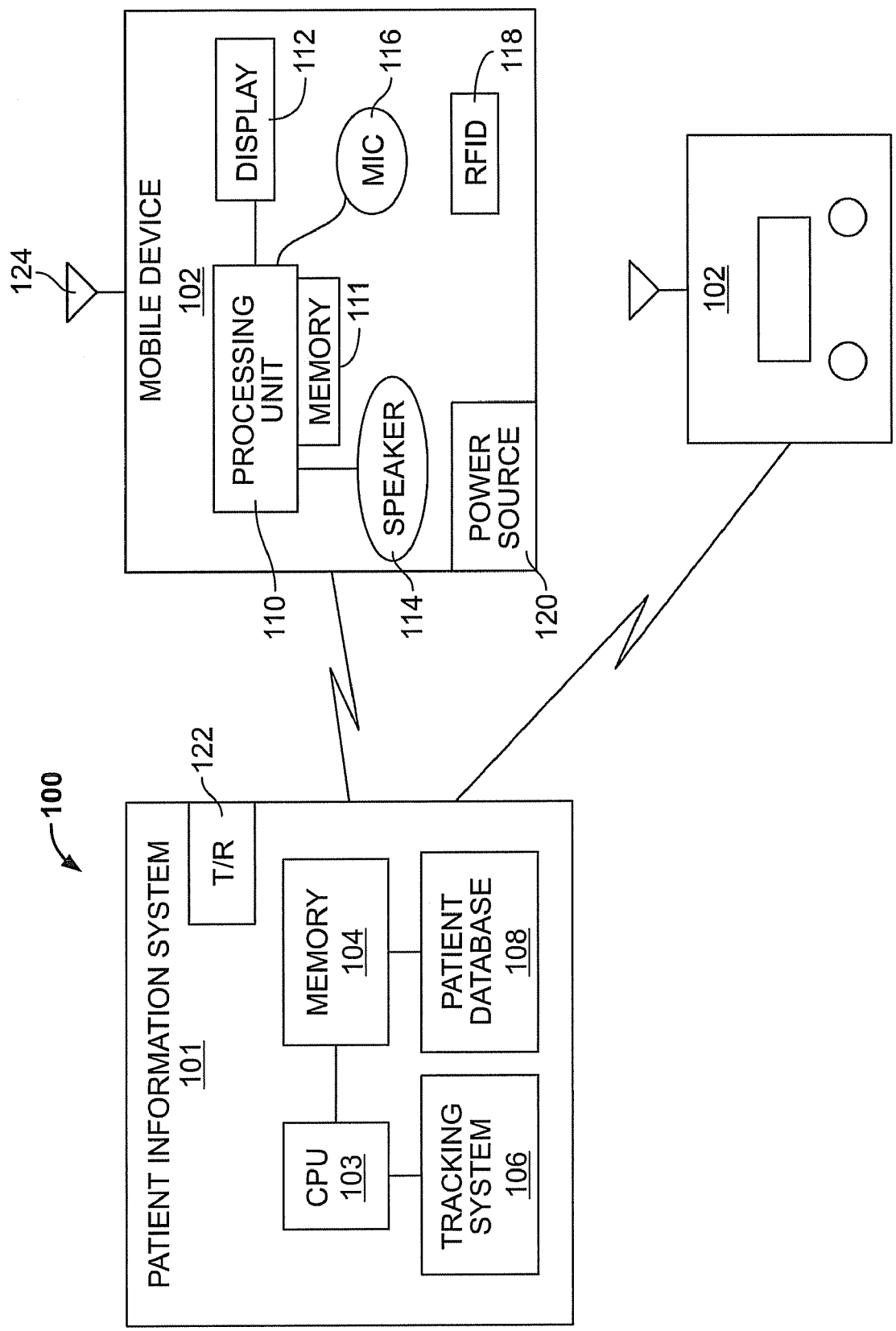
FIG. 1 illustrates a schematic of a patient management system according to an embodiment of the present invention.

The foregoing summary, as well as the following detailed description of certain embodiments of the present invention, will be better understood when read in conjunction with the appended drawings. For the purpose of illustrating the invention, there is shown in the drawings, certain embodiments. It should be understood, however, that the present invention is not limited to the arrangements and instrumentality shown in the attached drawings.

DETAILED DESCRIPTION OF THE INVENTION

FIG. 1 illustrates a schematic of a patient management system 100 according to an embodiment of the present invention. The patient management system 100 includes a patient information system 101 and a plurality of mobile devices 102. The mobile devices 102 are issued to patients within a medical care facility to efficiently direct and instruct the patients with respect to medical care events, such as x-ray procedures, doctor visits, blood work, and the like.

The patient information system 101 may be a main records information system within a medical care facility and may include a radiology information system, catheter lab information system, chemistry (e.g., blood, urine, etc.) information system, and various other components of the medical care facility. The patient information system 101 may electronically store all patient records within the medical care facility.

The patient information system 101 includes a central processing unit 103 in electrical communication with a memory 104 and a tracking system 106. The memory 104 may store instructions for operation of the patient information system 100. The memory 104 may include, or be in electrical communication with, a patient database 108 that stores all patient records.

The mobile device 102 may be a handheld device that is issued to a patient upon arrival at the medical care facility. The mobile device 102 includes a processing unit 110 electrically connected to a display 112, a speaker 114 and a microphone 116. The processing unit 110 may also be connected to a memory 111 that stores instructions for operation of the mobile device 102. The processing unit 110 is configured to operate the mobile device 102 as discussed below. The mobile device 102 also includes one or more input buttons (not shown in FIG. 1). The mobile device 102 may also include an embedded radio frequency identification tag 118 or the like that allows the tracking system 106 of the patient information system 100 to track the location of the mobile device 102. The mobile device 102 also includes a power source 120, such as a battery.

In operation, when a patient arrives at a medical care facility, the patient is issued a mobile device 102. For instance, the patient may be issued the mobile device 102 at the reception area of the medical care facility. Upon receiving the mobile device 102, the patient inputs basic identification information and perhaps a password. The password provides additional security for a patient, thereby minimizing the possibility that another person can pose as the patient. The patient may be told the password before the patient arrives at the medical care facility.

Optionally, instead of a password, the mobile device 102 may include a biometric input member. The patient may be instructed to input a biometric identifier, such as a fingerprint, that is compared with stored biometric data. Thus, the patient may log in through a biometric identifier, instead of a password.

Once logged into the system, the mobile device 102 communicates with the patient information system 101. The patient information system 101 accesses the stored records for the patient within the patient database 108. Once the patient and his/her records are matched within the patient database 108, the patient information system 100 transmits, such as through an integral transceiver 122, data regarding instructions and directions to the mobile device 102. The mobile device 102 receives the data through an integral transceiver 124 and the information is displayed on the display 112 of the mobile device 102. For example, the patient information system 101 may inform the patient, through the mobile device, to proceed to the radiology lab and provide appropriate directions to the patient.

As the patient moves within the medical facility, the tracking system 106 continually tracks the location of the patient through the mobile device 102. As noted above, the RFID tag 118 allows the tracking system to provide real time tracking of the mobile device 102. As the mobile device 102 is tracked, the directions may be continually updated. For example, if a patient is to report to a doctor's office, the mobile device 102 may display initial directions to the patient with respect to the reception area. As the patient proceeds according to those directions from the reception area, the display 112 may provide updated directions as the patient gets closer to the eventual location.

Figure 2:
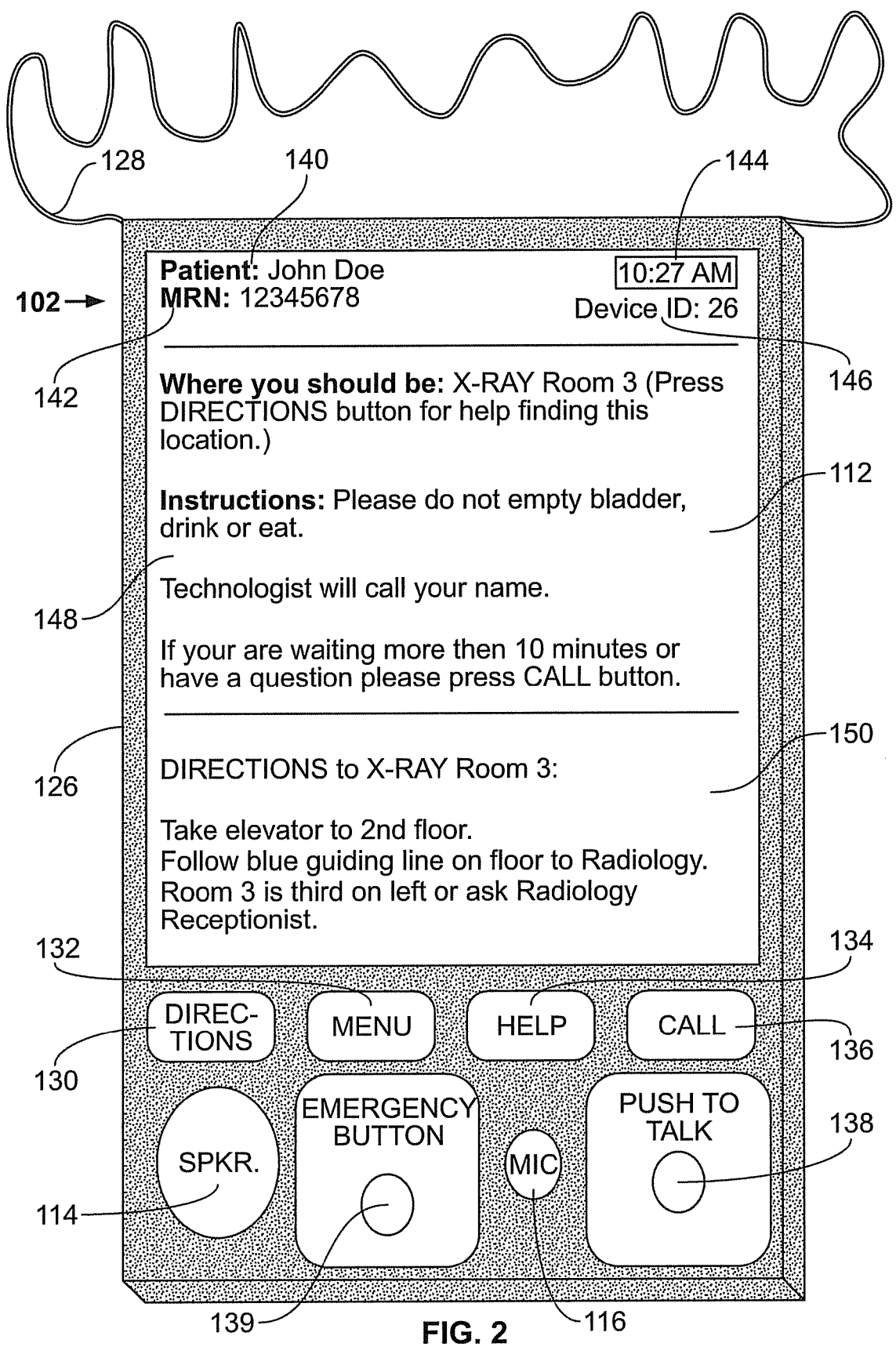
FIG. 2 illustrates a front view an interactive mobile device according to an embodiment of the present invention.

FIG. 2 illustrates a front view the interactive mobile device 102 according to an embodiment of the present invention. The mobile device 102 includes a housing 126 that is configured to fit within a patient's hand, be clipped to a belt, or hang around a patient's neck through a strap 128. The mobile device 102 may also be configured to be removably secured to a patient's bed, if the patient stays at the medical facility over an extended period of time (i.e., an "in-patient"). In general, the mobile device 102 may be approximately the same size as a mobile phone.

As noted above, the mobile device 102 includes the display 112, the speaker 114 and the microphone 116. The mobile device 102 may also include a volume control (not shown). The display 112 may be a touch-sensitive screen that allows a patient to touch certain areas on the screen, such as virtual buttons. Optionally, the mobile device 102 may include a keypad.

The mobile device 102 includes a plurality of buttons that may be located on the face of the housing 126 or may be virtual buttons on the display 112. A directions button 130 may be engaged to direct the patient to a particular location.

As noted above, the directions shown on the display may be continually updated based on a patient's current position within the medical facility.

A patient may press a menu button 132, which may then show a variety of menu options on the display 112. For example, a general menu display may include directions to a particular location, dietary restrictions, procedures to be taken, results of lab work, and various other options.

If lost or confused, the patient may press the help functions button 134. In this instance, the display may prompt a variety of frequently asked questions. For example, the display 112 may show questions asking whether the patient is lost, understands English, or the like. If the patient is having difficulty understanding English, the patient may switch to another language for display. For example, the display 112 may show virtual buttons that indicate various languages such as English, Espanol, Francais, etc. The patient may touch the virtual button of the language with which he/she is most comfortable. Optionally, when the help function 134 is pressed, the mobile device 102 may automatically call a receptionist who may answer any questions the patient may have.

The patient may also press the call button 136 to call reception or an operator. When the patient presses the call button 136, the display 112 may show a list of personnel, such as reception, radiologist, general doctor, etc. The patient may then touch the desired virtual button to speak with that particular person. The call button 136 may allow the patient to contact a variety of personnel within the medical care facility. The patient may listen to the other person through the speaker 114 and speak to that person through the microphone 116. For example, the patient may press the talk button 138 to activate the microphone 116.

The mobile device 102 may also include an emergency button 139. If the patient experiences an emergency, the patient presses the emergency button 139, at which point the mobile device 102 automatically contacts an operator who can speak to the patient through the mobile device 102. Further, if the patient is non-responsive during the call, the operator may instruct personnel to immediately proceed to the tracked location of the mobile device 102.

Referring to FIGS. 1 and 2, once the patient logs into the patient management system 100, the patient information system 101 matches the patient with information in the patient database 108. The information in the patient database 108 includes medical history, procedures to be performed, locations to where the patient is to proceed, and instructions regarding the procedures (e.g., dietary restrictions for a cholesterol screening). This information may be input by a care provider before the patient arrives at the medical care facility.

After the patient is logged in and the patient information system 101 matches the patient with information in the patient database, the patient information 101 transmits various types of information to the mobile device 102. As shown in FIG. 2, the display 112 shows the patient's name 140, patient identification number 142, a clock 144, a device identification number 146, an instructions field 148 and a directions field 150.

The patient name 140 allows the patient to verify that the mobile device 102 is properly issued to the patient. The instructions field 148 informs the patient where he/she should proceed and instructions regarding the procedure to be performed. For example, the patient may be informed not to eat or drink due to the nature of the procedure to be performed. Also, the mobile device informs the patient what will occur when the patient arrives at the location. For example, the patient may be instructed that a technologist will call the patient's name. If the patient is not called within a certain amount of time, the patient is instructed to press the call button 136.

The directions field 150 provides directions to the patient. The directions may be continually updated based on the patient's changing location within the medical facility. That is, the tracking system 106 tracks the location of the mobile device 102 of the patient and updates the directions in real time. Referring to FIG. 2, in particular, once the patient takes the elevator to the second floor, that portion of the directions may be removed from view so that the patient knows to follow the blue guiding line on the floor. If the patient becomes lost, the directions are appropriately updated to guide the patient to the proper location.

Once the patient arrives at the appropriate location, the patient is checked in as present. Because the mobile device 102 is tracked through the tracking system 101, there is no need for the patient to formally check in when he/she arrives at a particular location. Instead, the tracking system 106 determines that the patient is at a particular location and automatically sends a message to the technologist that the patient is present.

Further, instead of filling out paper information forms, the patient may press the menu button 132 and gain access to an information input mode. In this mode, the patient may provide personal, insurance and other information through the mobile device 102, instead of relying on filling out paper forms and having an employee of the medical facility input that information into the patient database 108. For example, the patient may input information into the mobile device 102 through the touch-sensitive display 112 or through a separate keypad. That information is then wirelessly transmitted to the patient information system 101, where it is stored in the patient database 108. Thus, the extra steps of filling out paper forms and then having an employee input that information into the database 108 are obviated, thereby making the information input stage more efficient. That is, the patient him/herself directly inputs this information without relying on a middleman to interpret his/her handwriting and input the information for him/her.

Also, if a care provider decides to change a procedure or check-up location, the care provider may input instructions into the patient information system 101. The patient information system 101 may then transmit the change in location to the mobile device 102, which then displays the updated information to the patient. The patient is therefore unlikely to report to an improper location or an outdated (in terms of a changed procedure) location. Thus, the system 100 ensures that the patient is cared for efficiently, even if a procedure location is changed.

If the patient leaves the medical care facility with the mobile device 102, the tracking system 106 detects that the mobile device 102 is offsite. In this situation, the patient information system 101 transmits a message to the mobile device 102 indicating that the patient needs to return to the mobile device 102 to the reception area. The message may include an audible ringing, buzzing or other such tone that is broadcast through the speaker 114. Thus, the patient is unlikely to accidentally carry the mobile device 102 away from the medical care facility.

Also, after the patient is finished with a procedure(s), the mobile device 102 may instruct the patient to return the mobile device 102 to reception. If the tracking system 106 detects that the patient is moving away from reception, or toward an exit, within the medical care facility, the return alert described above may be transmitted to the mobile device 102 in order to remind the patient to return the mobile device 102 to reception.

Figure 3:
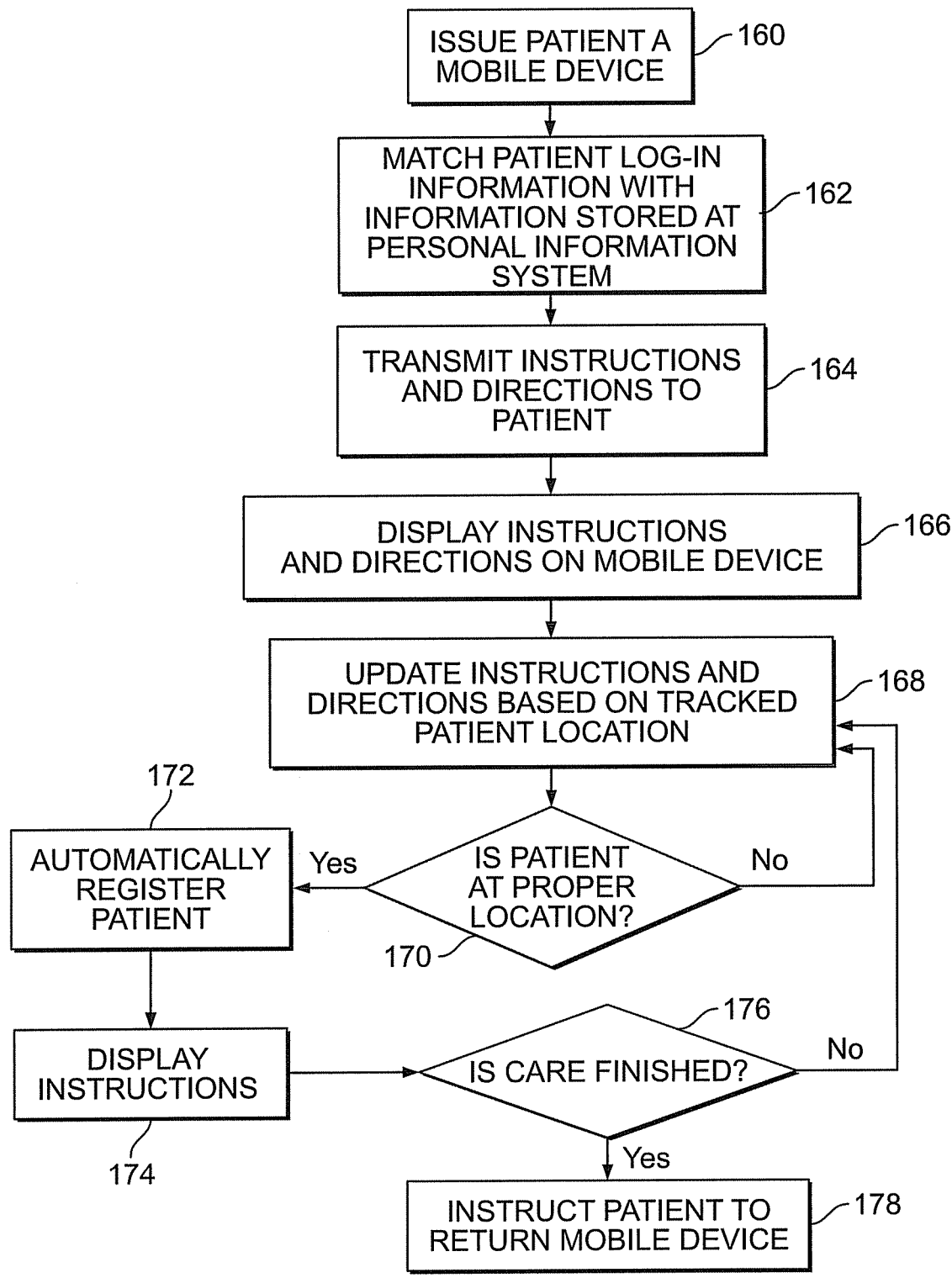
FIG. 3 illustrates a flow chart of a patient care event according to an embodiment of the present invention.

FIG. 3 illustrates a flow chart of a patient care event according to an embodiment of the present invention. At 160, the patient is issued a mobile device, such as when a patient reports at a reception area of a medical care facility. When the patient receives the mobile device, the patient logs in, such as by entering information through the mobile device when prompted on the display screen. A password and/or biometric identifier may be used to provide additional security.

At 162, the log in information is transmitted to the patient information system and matched with information stored in a patient database. Based on the matched information, the personal information system transmits instructions and directions to the mobile device at 164. The mobile device displays the instructions and directions to the patient at 166.

At 168, as the patient moves through the medical facility, the displayed instructions and/or directions are updated based on the tracked patient location. At 170, the patient information system determines whether the patient is at the proper location. If so, the patient is automatically registered at 172. If not, the method returns to 168.

Once registered, the mobile device may display a message that informs the patient that he/she has been registered. The mobile device then displays instructions regarding the particular medical care event at 174. For example, the patient may be instructed to wait until a technologist calls his/her name.

At 176, the method determines whether the care event is finished. If not, the method returns to 168. If the care event is finished, the patient is instructed to return the mobile device 178 and directions are displayed to guide the patient to the return location.

Embodiments of the present invention manage a medical care episode from the perspective of the patient, as opposed to the care provider. Because the system and method are patient-centric, the medical care episode proceeds efficiently with less input by the care provider. As such, the care provider may focus more energy on caring for patients. In general, embodiments of the present invention expand the scope of the medical workflow management to directly involve the patient.

Embodiments of the present invention reduce patient confusion and frustration. The mobile device allows a patient to be informed of where he/she should be, and how to get there.

Embodiments of the present invention provide a more efficient medical care event. The mobile device allows a patient to directly input personal and insurance information, without the need to write such information and then have that information input by a medical facility employee. As such, the registration process is quicker and more accurate than in previous settings.

Embodiments of the present invention allow a patient to quickly alert the medical care facility of an emergency condition. The patient may press the emergency button on the mobile device, instead of relying on finding a separate and distinct telephone within the facility.

Embodiments of the present invention also ensure that a patient is matched with appropriate records. The patient and care provider can easily see if the mobile device is issued to the proper patient. Plus, the mobile device is directly linked with the patient database. As such, there may not be paper records to match with a particular patient.

Embodiments of the present invention provide a system and method for assisting patients that may be lost within the facility. If lost, the patient may view directions on the mobile device. The directions may be continually updated through the tracking system. Moreover, the instructions and directions may be dynamically updated if a care provider decides to change the scheduling of care event episodes.

Additionally, embodiments of the present invention provide a system and method that allows a patient to navigate through a medical care facility even if he/she is not fluent with the languages posted on signs within the facility. The mobile device may be switched to provide instructions and directions in a variety of languages.

While the present invention has been described with reference to certain embodiments, it will be understood by those skilled in the art that various changes may be made and equivalents may be substituted without departing from the scope of the invention. In addition, many modifications may be made to adapt a particular situation or material to the teachings of the invention without departing from its scope. Therefore, it is intended that the invention not be limited to the particular embodiments disclosed, but that the invention will include all embodiments falling within the scope of the appended claims.

The invention claimed is:

1. A mobile device configured to instruct and direct a patient within a medical care facility, the mobile device comprising:
    a main housing configured to be conveyed by the patient within the medical care facility;
    a display positioned on said main housing;
    a tracking device configured to be tracked by a patient information system;
    a processor in communication with said display; and
    a transceiver allowing bi-directional communication between the mobile device and the patient information system, said transceiver being configured to receive patient-specific directions and instructions regarding a medical care event within the medical care facility, wherein the patient-specific directions and instructions are transmitted from the patient information system, said processor being operable to show the patient-specific directions and instructions on said display, and wherein the patient-specific directions relate to a position of the mobile device with respect to locations within the medical care facility.

2. The mobile device of claim 1, wherein the patient-specific directions and instructions are updated based on a tracked location of the mobile device within the medical care facility.

3. The mobile device of claim 1, wherein said display comprises a touch-screen that is configured to allow the patient to make selections by touching virtual buttons on said touch-screen.

4. The mobile device of claim 1, comprising an actual and/or virtual directions button that is configured to allow the patient to acquire directions to a particular location.

5. The mobile device of claim 1, comprising an actual and/or virtual menu button.

6. The mobile device of claim 1, comprising an actual and/or virtual call button.

7. The mobile device of claim 1, comprising an actual and/or virtual emergency button.

8. The mobile device of claim 1, comprising a speaker and a microphone.

9. The mobile device of claim 1, wherein said processor is operable to show a patient name and identification number on said display.

10. The mobile device of claim 1, wherein said tracking device is a radio frequency identification tag.

11. The mobile device of claim 1, wherein the patient-specific directions orient and guide the patient with respect to the locations within the medical care facility.

12. The mobile device of claim 1, wherein the patient-specific directions inform the patient where to go, and how to get there, within the medical care facility.

13. A system configured to instruct and direct a patient within a medical care facility, the system comprising:
   a patient information subsystem, said patient information subsystem comprising:
      a central processing unit;
      a patient database in communication with said central processing unit;
      a tracking subsystem in communication with said central processing unit; and
      a first transceiver in communication with said central processing unit;
   a mobile device configured to be conveyed by the patient within the medical care facility, said mobile device being separate and distinct from said patient information subsystem, said mobile device comprising:
      a display positioned on said main housing;
      a tracking device configured to be tracked by said tracking subsystem;
      a processor in communication with said display; and
      a second transceiver allowing bi-directional communication between said mobile device and said patient information system, said second transceiver receiving patient-specific directions and instructions regarding a medical care event within the medical care facility, wherein the patient-specific directions and instructions are transmitted from said central processing unit through said first transceiver, said processor being operable to show the patient-specific directions and instructions received from the patient information subsystem on said display, and wherein the patient-specific directions relate to a position of said mobile device with respect to locations within the medical care facility.

14. The system of claim 13, wherein the patient-specific directions and instructions are updated based on said tracking subsystem tracking said mobile device within the medical care facility.

15. The system of claim 13, wherein said display comprises a touch-screen that is configured to allow the patient to make selections by touching virtual buttons on said touch-screen.

16. The system of claim 13, wherein said mobile device comprises a plurality of actual and/or virtual buttons that are configured to: (a) allow the patient to acquire directions to a particular location, (b) gain access to menu options, (c) call medical care facility personnel, and (d) alert the medical facility personnel of an emergency condition.

17. The system of claim 13, wherein said mobile device comprises a speaker and a microphone.

18. The system of claim 13, wherein said processor is operable to show a patient name and identification number on said display.

19. The system of claim 13, wherein said tracking device is a radio frequency identification tag.

20. The system of claim 13, wherein the patient-specific directions orient and guide the patient with respect to the locations within the medical care facility.

21. The system of claim 13, wherein the patient-specific directions inform the patient where to go, and how to get there, within the medical care facility.

22. A method of instructing and directing a patient within a medical care facility with respect to a medical care event, the method comprising:
   matching patient information input by the patient into a mobile device with data stored in a patient information system, wherein the patient information system is separate and distinct from the mobile device;
   transmitting instructions and directions from the patient information system to the mobile device based on said matching;
   displaying the instructions and directions on the mobile device; and
   updating the instructions and directions based on one or both of the location of the patient within the medical care facility and/or a stage of the medical care event.

23. The method of claim 22, comprising receiving personal and insurance information directly input by the patient into the mobile device at the patient information system.

24. The method of claim 23, comprising automatically registering the patient for the medical care event when the patient arrives at the proper location and after said receiving.

25. The method of claim 22, comprising alerting the patient to return the mobile device when the patient moves out of a predetermined area.

26. The method of claim 22, wherein the directions orient and guide the patient with respect to the locations within the medical care facility.

27. The method of claim 22, wherein the directions inform the patient where to go, and how to get there, within the medical care facility.

* * * * *